United States Patent

An et al.

[11] Patent Number: 5,545,211
[45] Date of Patent: Aug. 13, 1996

[54] STENT FOR EXPANDING A LUMEN

[75] Inventors: Sung-soon An, Seoul; Suk-jae Lee, Kyungki-do, both of Rep. of Korea

[73] Assignee: Sooho Medi-Tech Co., Ltd., Seoul, Rep. of Korea

[21] Appl. No.: 310,878

[22] Filed: Sep. 22, 1994

[30] Foreign Application Priority Data

Sep. 27, 1993 [KR] Rep. of Korea .................. 93-19771

[51] Int. Cl.[6] ............................................. A61F 2/06
[52] U.S. Cl. ........................ 623/1; 606/191; 606/198
[58] Field of Search ................... 623/1, 12; 606/191, 606/192, 193, 194, 195; 428/364, 369, 375, 379, 392

[56] References Cited

U.S. PATENT DOCUMENTS

| | | | |
|---|---|---|---|
| 4,580,568 | 4/1986 | Giantureo | 128/345 |
| 4,596,577 | 6/1986 | Sato | 623/1 |
| 4,733,665 | 3/1988 | Palmaz | 128/343 |
| 4,856,516 | 8/1989 | Hillstead | 128/343 |
| 4,886,062 | 12/1989 | Wiktor | 128/343 |
| 5,019,090 | 5/1991 | Pinchuk | 606/194 |
| 5,035,706 | 7/1991 | Giantureo et al. | 606/198 |
| 5,064,435 | 11/1991 | Porter | 623/12 |
| 5,116,360 | 5/1992 | Pinchuk et al. | 623/1 |
| 5,133,732 | 7/1992 | Wiktor | 606/195 |
| 5,151,105 | 9/1992 | Kwan-Gett | 623/1 |
| 5,167,614 | 12/1992 | Tessmann et al. | 604/8 |
| 5,192,311 | 3/1993 | King et al. | 623/1 |
| 5,330,500 | 7/1994 | Song | 606/198 |

FOREIGN PATENT DOCUMENTS

| | | |
|---|---|---|
| 0177330 | 4/1985 | European Pat. Off. . |
| 1766921 | 1/1970 | Germany . |
| WO92/06734 | 4/1992 | WIPO ................. 606/194 |

Primary Examiner—Gary Jackson
Assistant Examiner—Mark S. Leonardo
Attorney, Agent, or Firm—Christie, Parker & Hall, LLP

[57] ABSTRACT

A stent for expanding lumens, formed of a wire member which has a zigzag configuration, first and second straight sections and a plurality of bends cross-linked with each other to form a plurality of turns. The stent need not provide means for connecting each wire member. The elasticity of the stent is uniform. The position of the stent in a body cavity is maintained since the longitudinal change of the stent is very small. Also the stent provides means for preventing restenosis of the lumens.

10 Claims, 5 Drawing Sheets

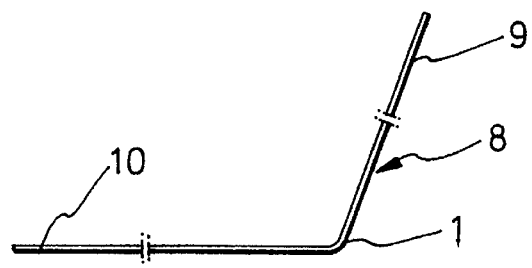
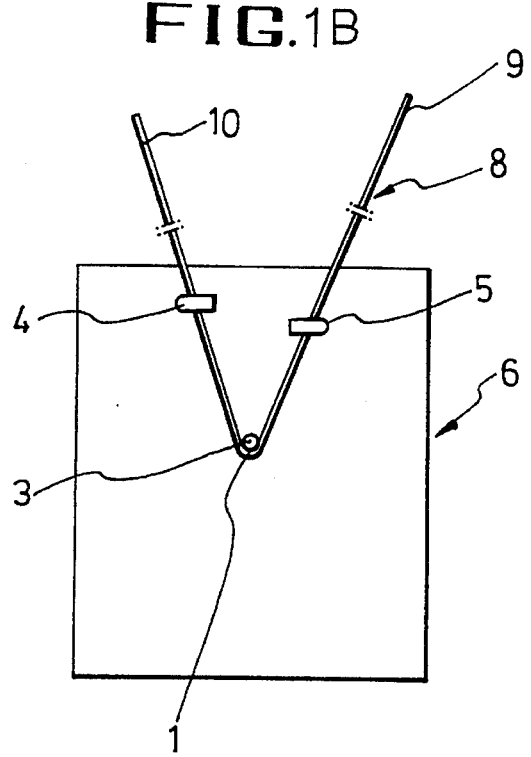
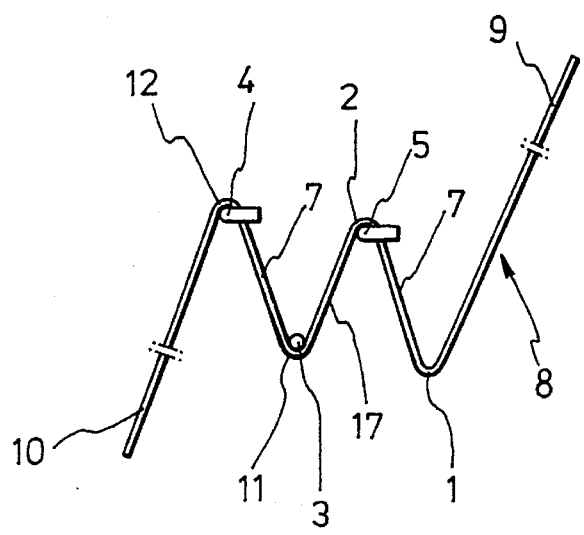
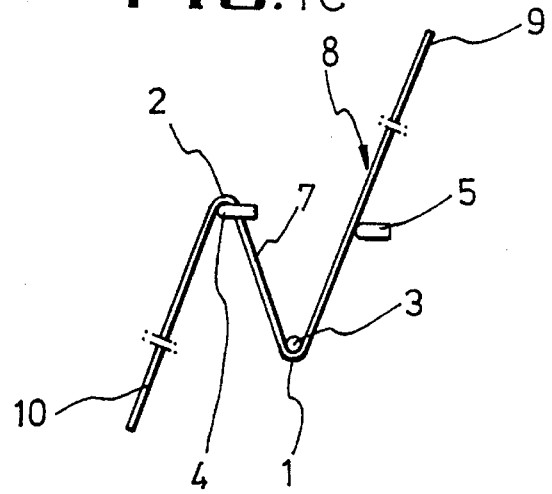

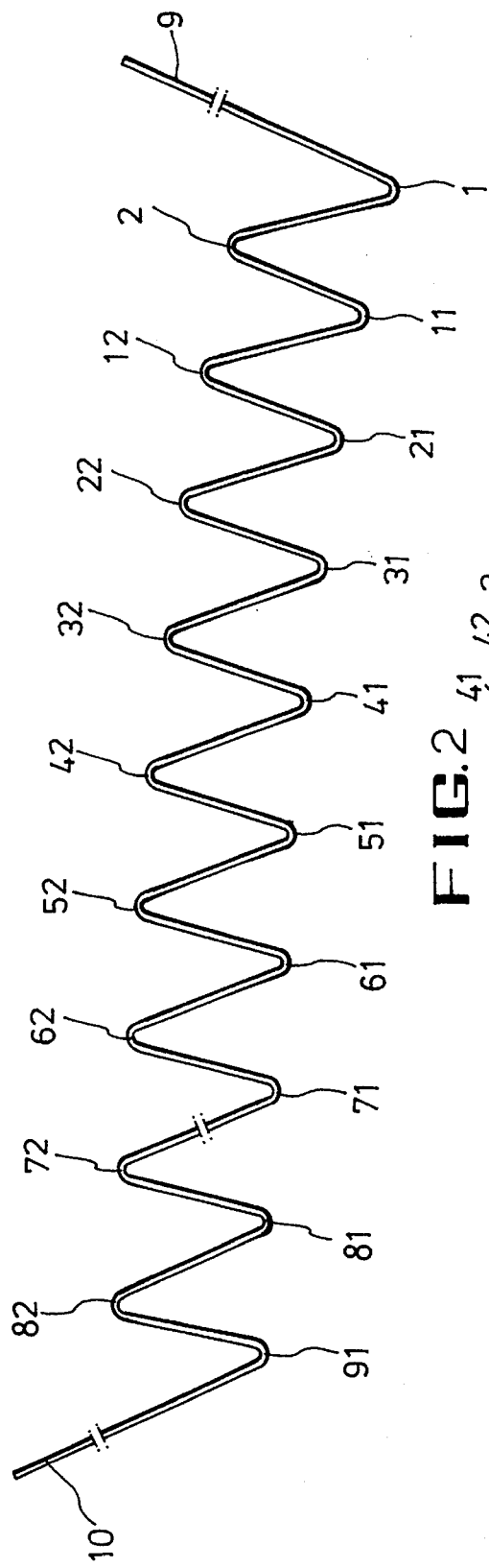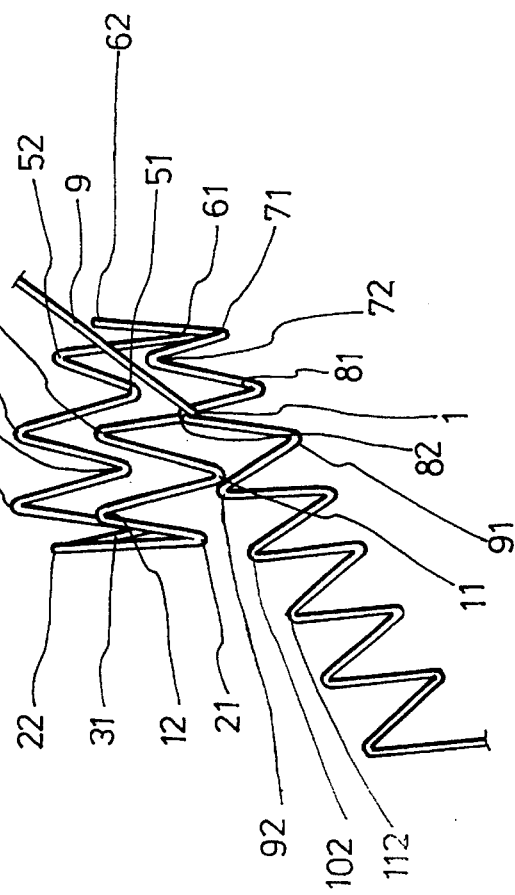

5,545,211

STENT FOR EXPANDING A LUMEN

FIELD OF THE INVENTION

The present invention relates to a stent and, more particularly, to a self-expandable stent for expanding the lumens of a blood vessel or liver in case these are constricted.

BACKGROUND OF THE INVENTION

In many situations, a device is required for expanding a constricted passageway of a blood vessel or the liver, or maintaining an open passageway through a vessel portion. Such situation arise, for example, when the blood does not flow smoothly or the passageways of the vessel portion are constricted due to arteriosclerosis or the growth of a tumor.

Expanding the passageway for smooth flowing is needed in such cases, and for this purpose devices for pushing an elastic body which can expand by itself in the constricted passageway are proposed and used. The elastic body is called a stent, for example, a wire formed in a closed zigzag configuration, joined by a plurality of bends and wound cylindrically, as can be seen in EP 0177330.

Since each section of the stent of the above structure is formed by a plurality of connecting members linking section to each other to be used in practical use. Thus, when the stent is placed in a bent portion of the lumen, a space is formed between a bend of a first stent section and a corresponding bend of a second stent section. The space allows restenosis of passageways or ducts in the body.

To avoid the use of numerous connecting members, U.S. Pat. No. 4,733,665 discloses a graft which is formed by a tubular shaped member having first and second ends and a wall disposed between the first and second ends. The wall surface is formed by a plurality of intersecting elongate members, at least some of the elongate members intersecting with one another intermediate the first and second ends of the tubular shaped member. In the graft of this configuration, since a plurality of elongate members only intersect with each other, the elasticity of the graft is formed only in the first and second ends of the tubular shaped member and it is weak between the ends.

SUMMARY OF THE INVENTION

Accordingly, it is an object of the present invention to provide a stent which can form a passageway for blood in its bent state yet prevent tissue from penetrating.

Another object of the present invention is to provide a stent which maintains its length in case of constriction or expansion of the stent.

A further object of the present invention is to provide a stent having a uniform elasticity.

In order to achieve the above objects in one embodiment, the present invention provides a stent formed of one wire member which has a zigzag configuration which is then spiraled into turns, and bends of the zigzag are cross-linked with each other at adjacent turns. In addition, in a preferred embodiment, the ends of the wire are bent and woven between turns. The tips of the wire are then hooked around an intermediate turn.

The foregoing, other objects and advantages of the present invention will become apparent from the following detailed description made in connection with the accompanying drawings.

BRIEF DESCRIPTION OF THE DRAWINGS

FIGS. 1A to 1E are views for assistance in explaining one method of manufacture of the stent for expanding lumens according to the present invention.

FIG. 2 is a view for showing a stage of manufacturing the stent for expanding lumens according to the present invention.

DETAILED DESCRIPTION OF THE INVENTION

Figure 3:
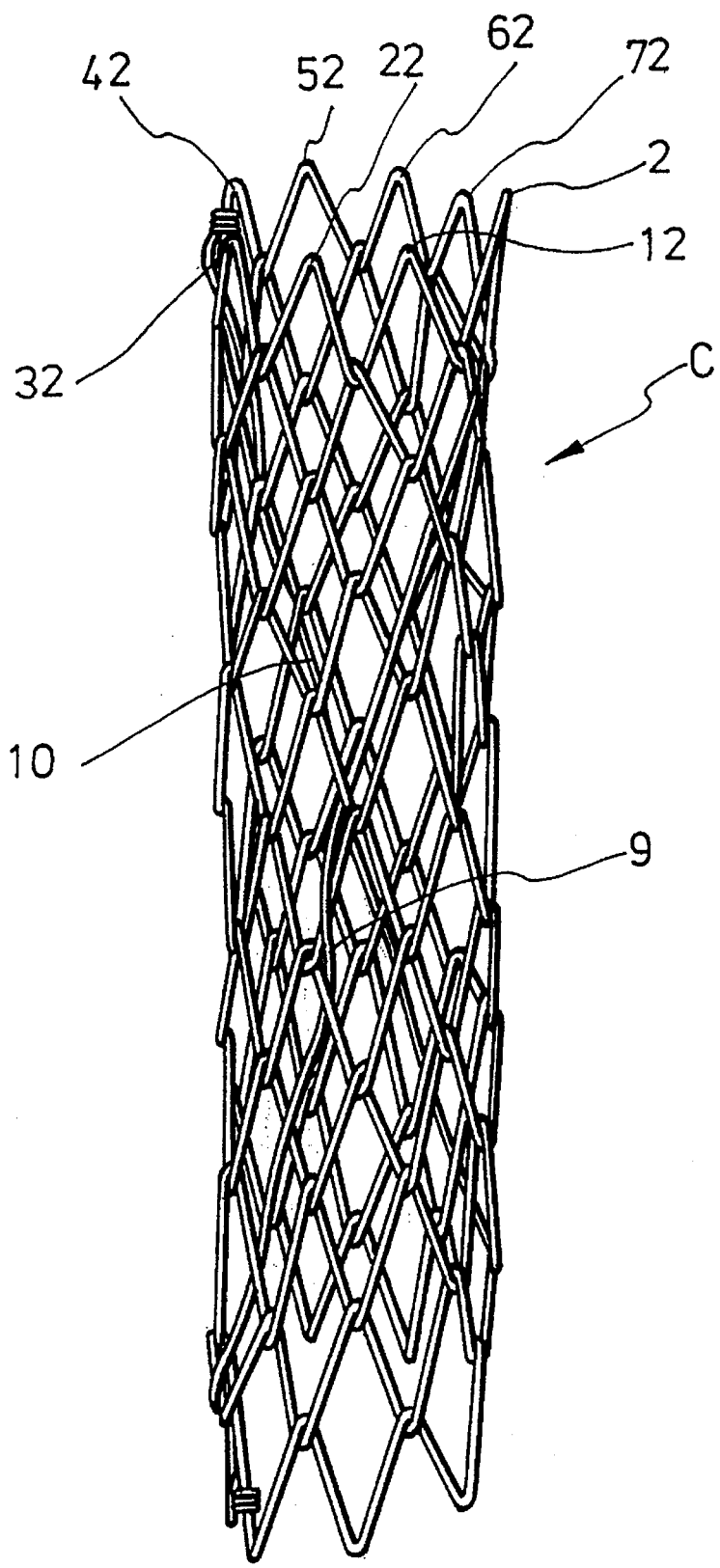
FIG. 3 is a perspective view of the stent for expanding lumens according to the present invention.
Figure 4:
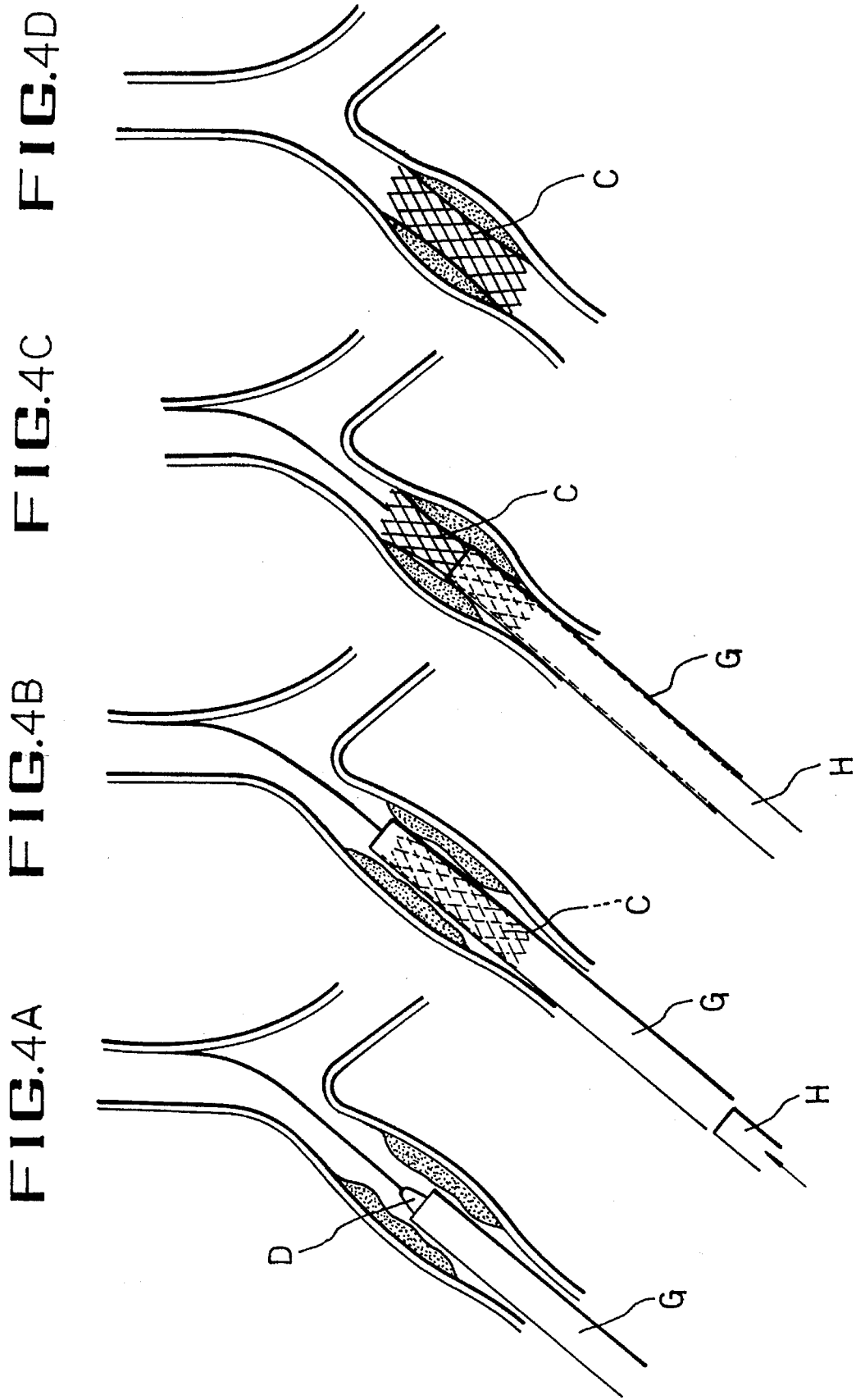
FIGS. 4A to 4D are views showing steps for implantation of the stent into a lumen of a blood vessel or of the liver.
Figure 5:
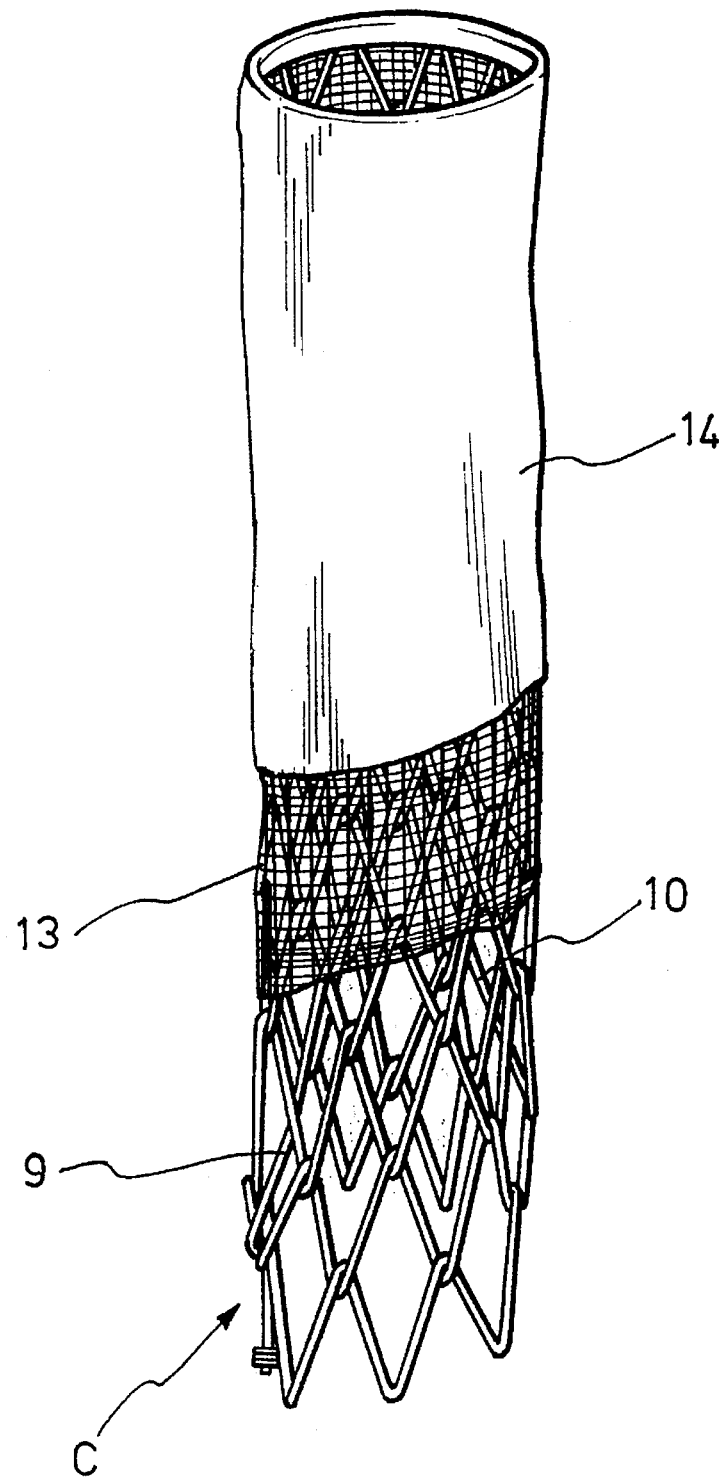
FIG. 5 is a perspective view of another embodiment according to the present invention in which the elastic body is wrapped in a mesh and coated by a silicon rubber.

Explanation is given in accordance with the drawings. Referring to FIG. 1A, a wire 8 having upper and lower ends 9 and 10, preferably made of stainless steel, is bent near the upper end portion 9 to form a first bend 1 which is referred to as a lower bend. The first bend 1 is hooked around a first pin 3 on a jig 6, the left portion of the wire 8 is hung inside a second pin 4, and the right portion of the wire 8 is hung on a third pin 5, as shown in FIG. 1B.

The distance between the first and second pins 3 and 4 is longer than that between the first and third pins 3 and 5. The second and third pins 4 and 5 are different from the first pin 3. That is, the second and third pins 4 and 5 are bent horizontally and have an inner space for the wire to be inserted. The wire 8 is inserted into the space formed by the bent pin 4 and the wire 8 is bent around the second pin 4 to form a second bend 2 which is referred to as an upper bend. Then, the wire 8 is twisted to a predetermined angle, which helps the wire 8 to form a desirable shape.

A first straight section 7 is defined as the portion of the wire 8 between the first and second bends 3 and 4, as shown in FIG. 1C.

Another second bend 2 is hung on the third pin 5 and the left portion of the second bend 2 is bent about another first pin 3 to form a third bend 11 and a second straight section 17, as shown in FIG. 1D. The third bend 11 belongs to the category of lower bends.

Since the first straight section 7 is formed between the first and second pins 3 and 4 and the second straight section 17 is formed between the first and third pins 3 and 5, the first straight section 7 is longer than the second straight section 17. Further, the first straight section 7 is twisted from the second straight section 17 by a predetermined angle because of the second and third pins 4 and 5, the shapes of which are not necessary but help to form a twisted angle between the first and second straight sections 7 and 17.

If such a process is continued, as illustrated in FIG. 1E, a wire of a zigzag configuration, which has a plurality of the first and second straight sections 7 and 17, the lower bends 1, 11, 21, 31, . . . , and the upper bends 2, 12, 22, 32, . . . , is formed. However, both end portions 9 and 10 of the wire 8 are left unbent.

A number of bends is selected for a first turn of the zigzag structure of FIG. 1E and the upper bends of such turn are cross-linked with the corresponding lower bends of the next turn, as shown in FIG. 2. Eventually, the wire 8 having a plurality of spiral bends is formed into a cylindrical elastic body, as shown in FIG. 3.

That is, referring back to FIG. 2, in case the number of bends for a turn is 18, the 18th bend 82, which is one of the upper bends 2, 12, 22, 32, 42, 52, 62, 72, 82, 92, 102, . . . , is cross-linked (or hooked) with the first bend 1. The 20th bend 92 which is also one of the upper bends is cross-linked or hooked with a corresponding bend from the prior turn, namely the third bend 11 which is one of the lower bends. The 22nd bend 102 is stuck into the 5th bend 21 from inside to outside, the 24th bend 112 is stuck into the 7th bend 31. The next turn, or a third turn is formed the same way as the first and second turns. That is, each of the upper bends of the third turn is cross-linked with a corresponding lower bend of the second turn.

Such a process is continued until a desirable height of the stent, or a desirable number of turns is obtained. Then, the upper bends; 2nd, 4th, 6th, 8th, . . . , and 18th bends are arranged spirally, the lower bends; the 1st, 3rd, 5th, 7th, . . . , and 17th bends are also arranged spirally, and the cylindrical body is obtained as shown in FIG. 3.

It is desirable to make the stent about 10 cm long. Each of the straight sections is desirable to be about 0.9 cm and the first straight sections 7 are slightly longer than the second straight sections 17. However, the length and the diameter of the stent are determined in accordance with the characteristics of the wire and the lumen where the stent is applied.

At this time, both ends 9 and 10 of the wire 8 are disposed at a top position and at a bottom position, respectively. The upper end 9 of the stent, or the wire 8 extends diagonally in the direction of the bottom of the stent in such manner that it weaves in and out of every other turn or every third turn of the stent from inner side to outer side to inner side and from the outer side of each turn. At last the upper end 9 is fixed by being wound around a straight section of a certain turn. The lower end 10 extends in the direction of the first turn and is wound around a straight section of a certain turn in similar manner as the upper end 9. As a matter of fact, it is of no use determining which end is defined as an upper end or lower end. This configuration of the end portions 9 and 10 restrains the deformation of the stent in every direction of the stent.

That is, in the stent according to the invention, bends are arranged spirally and bends are hooked with each other like a chain link fence or net, and both ends are formed in the above described way. Therefore, the bends of the stent do not project outside the whole structure even in case the stent is bent due to the linking of the turns to themselves, which means that the passageway where the stent according to the invention is applied maintains its opening and allows the blood to flow well. The interlinking of the adjacent bends from each of the various turns serves to regulate and limit expansion and contraction of the stent. Further, the interlinking distributes force evenly and the elasticity of the stent is more uniform than that of prior stents. Still further, deformation in the longitudinal direction is limited by the ends being anchored (bent around) and woven through the different turns of the stent.

Since the stent obtained by the above process may have a larger diameter than a practical one, it may be necessary to put it into a sleeve of desirable diameter and to treat it with heat.

Further, the stent may have to be wrapped in a mesh 13, and upper and lower hems of the mesh folded towards the inside of the stent, and both hems become respectively adhered or fixed to themselves through the stent's circumference or to the wire. The mesh is such that it is not exposed. It is preferable that the mesh 13 is made of nylon and the entire mesh has a coating 14 made of a silicon rubber. The coating 14 is formed as a hose-type membrane which is fitted around the stent and adhered to it. This structure is already disclosed in patent publication WO 92/06734 by Song, Ho-young and U.S. Pat. No. 5,330,500, hereby incorporated by reference.

The coating 14 can be formed directly around the wire 8, but to increase the adhesive force, the mesh 13 is preferred to be wrapped around the wire 8 inside of the coating 14. The effect of the coating is already known in this field, namely to prevent the growth of any tissue or to prevent restenosis.

The stent of this configuration is implanted in a blood vessel or other body cavity by means of an introducer or implantation will be described.

The introducer comprises an inner tube D and a guide G. The inner tube D helps the whole introducer to pass through the body cavity smoothly. The introducer with the inner tube D inserted on the guide G and the stent C between the guide G and the inner tube D is inserted to an aimed position of the body cavity at the first stage. The inner tube D is pulled out from the guide G, and the stent C in its compressed shape is pushed toward the opening of the guide G, the desired position, by a pusher H. Finally, the guide G is pulled out of the body cavity and only the stent C remains in the body cavity. Then the stent C expands and presses against the wall of the body cavity in order to maintain it open.

As described above, the stricture of a lumen due to the growth of the tissue can be prevented. In addition, the stent according to the present invention does not permit penetration of tissue of the lumen. Additionally, the stent has a greater elastic force than prior stents.

If compared with the stent disclosed in EP 0177330 issued to Cook Inc., which is connected by a plurality of straight line members in order to be used, the stent of the present invention does not change longitudinally even when the stent experiences compression or expansion. This means that the stent does not change its position when the stent is put in a desired position of the body cavity. Thus, once the stent is positioned exactly, there will be no deleterious expansion, contraction or movement of the stent.

While the invention -has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stent comprising a length of wire formed into a cylindrical configuration having a plurality of turns of a zigzag configuration consisting of a series of first and second straight sections joined by a plurality of bends consisting of lower and upper bends, wherein each of the first and second straight sections is defined between each of the upper and lower bends, the first straight section is longer than the second section and the upper bends of one turn are hooked with corresponding lower bends of an adjacent turn, and wherein the stent is resiliently compressible into a smaller first shape in which all of the straight sections are arranged side by side and closely adjacent one another for insertion into a passageway with the bends having a stress therein, the stent being resiliently expandable by release of said stress into a second shape in which all of the straight sections define a generally circular or cylindrical configuration for pressing against a wall of the passageway to maintain it open.

2. The stent according to the claim 1, wherein said wire comprises a first end portion and a second end portion, said first and second end portions of said wire being woven in and out of said plurality of turns of the wire in a direction towards opposite ends of the stent and fixed to one of said plurality of turns.

3. The stent according to the claim 1, wherein the top and bottom ends are fixed by being wound around the wire.

4. In combination, the stent of claim 1 and a tubular guide having said stent therein, said stent being resiliently compressed into said smaller first shape.

5. The stent according to claim 1, wherein the stent additionally comprises coating means for preventing a tumor from penetrating gaps created by the stent.

6. The stent according to claim 5, wherein the coating means is a mesh made of nylon.

7. The stent according to claim 6 wherein the mesh is additionally coated by a silicon rubber.

8. A stent comprising:

a single length of wire bent into a zigzag configuration comprising a series of straight sections joined by a plurality of bends, said plurality of bends comprising alternate peaks and valleys, each of said peaks being formed substantially identical to one another and each of said valleys being formed substantially identical to one another, the zigzag configuration being spirally wrapped about an axis into a plurality of turns, the axis forming a longitudinal axis of the stent, and wherein said peaks of one of said plurality of turns of the stent are interlocked with said valleys of an adjacent turn of the stent.

9. The stent of claim 8 wherein the wire comprises a first end portion and a second end portion, said first and second end portions being woven in and out of said plurality of turns extending towards opposite ends of the stent.

10. The stent of claim 9 wherein distal ends of the first and second end portions are hooked around a portion of one of said plurality of turns.

* * * * *